(12) United States Patent
Barre et al.

(10) Patent No.: US 8,426,648 B2
(45) Date of Patent: Apr. 23, 2013

(54) HYDROGENATION CATALYST, PARTICULARLY FOR CARBON DISULPHIDE

(75) Inventors: Patrice Barre, Jurancon (FR); Georges Fremy, Sauveterre (FR); Andre Lozowski, Lescar (FR)

(73) Assignee: Arkema France, Colombes (FR)

( * ) Notice: Subject to any disclaimer, the term of this patent is extended or adjusted under 35 U.S.C. 154(b) by 20 days.

(21) Appl. No.: 13/123,438

(22) PCT Filed: Oct. 22, 2009

(86) PCT No.: PCT/FR2009/052035
§ 371 (c)(1),
(2), (4) Date: May 10, 2011

(87) PCT Pub. No.: WO2010/046607
PCT Pub. Date: Apr. 29, 2010

(65) Prior Publication Data
US 2011/0213184 A1    Sep. 1, 2011

(30) Foreign Application Priority Data
Oct. 24, 2008    (FR) ...................... 08 57254

(51) Int. Cl.
*C07C 321/02*    (2006.01)
(52) U.S. Cl.
USPC .................................. 568/21; 568/18; 568/60

(58) Field of Classification Search ................... 568/71, 568/69, 70, 60, 18, 21; 502/314
See application file for complete search history.

(56) References Cited

U.S. PATENT DOCUMENTS

| 3,488,739 A | | 1/1970 | Venrooy |
| 3,880,933 A | * | 4/1975 | Kubicek .......................... 568/70 |
| 7,745,372 B2 | | 6/2010 | Li et al. |

FOREIGN PATENT DOCUMENTS

| EP | 0796656 A1 | | 9/1997 |
| FR | 2419281 A1 | | 10/1979 |
| FR | 2864102 | * | 12/2004 |
| FR | 2864102 A1 | | 6/2005 |

OTHER PUBLICATIONS

International Search Report received in PCT/FR2009/052035, mailed Apr. 8, 2010.

* cited by examiner

*Primary Examiner* — Johann R Richter
*Assistant Examiner* — Pancham Bakshi
(74) *Attorney, Agent, or Firm* — Smith, Gambrell & Russell, LLP

(57) ABSTRACT

The present invention relates to a hydrogenation catalyst, particularly useful for the hydrogenation of carbon disulphide ($CS_2$) to form methyl mercaptan ($CH_3SH$), and to a preparation method thereof. The present invention also relates to a method for continuously preparing methyl mercaptan by the catalytic hydrogenation of carbon disulphide, with a carbon disulphide conversion rate of 100%, and a methyl mercaptan selectivity of 100%.

24 Claims, No Drawings

HYDROGENATION CATALYST, PARTICULARLY FOR CARBON DISULPHIDE

The present invention relates to a hydrogenation catalyst of use in particular in the hydrogenation of sulfur-comprising compounds, especially those carrying an unsaturation of C=S type, and in particular in the hydrogenation of carbon disulfide ($CS_2$) to give methyl mercaptan ($CH_3SH$). The present invention also relates to the use of said catalyst in said hydrogenation reactions, to the process for the preparation of said catalyst and to the process for the preparation of methyl mercaptan by catalytic hydrogenation of carbon disulfide.

The reaction for the hydrogenation of $CS_2$ to give methyl mercaptan can be represented diagrammatically as follows:

$$CS_2 + 3H_2 \rightarrow CH_3SH + H_2S$$

The byproducts from this reaction are methane, by hydrogenolysis of $CH_3SH$, and dimethyl sulfide (DMS), by condensation of two $CH_3SH$ molecules.

This hydrogenation reaction, although known for decades, does not appear to form the subject of intensive research, if judged by the few patent publications available today.

For example, the U.S. Pat. No. 3,488,739 (The Sun Oil Company, 1970) describes a process for the preparation of methyl mercaptan and dimethyl sulfide from $CS_2$ and hydrogen using a hydrogenation catalyst (Aero-HDS-3A) which is a mixture of nickel and molybdenum oxides on alumina.

At 204° C., the $CS_2$ conversion is approximately 100% and the molar selectivities are 33% for $CH_3SH$ and 67% for DMS, with traces of methane.

At 177° C., the $CS_2$ conversion falls to 76 mol % and the molar ratio of the $CH_3SH$/DMS selectivities is 50/50.

The patent also mentions the possibility of recycling the $CH_3SH$ or DMS in order to promote the formation of one or other of these compounds. However, such a recycling results in the formation of not insignificant amounts of methane.

The U.S. Pat. No. 3,880,933 (Phillips, 1975) describes a process for the catalytic hydrogenation of $CS_2$ to give methyl mercaptan in the presence of hydrogen sulfide ($H_2S$). The catalyst used is a mixture of cobalt and molybdenum oxides on alumina (Aero-HDS-2).

The reaction temperature mentioned is between 230° C. and 260° C., the reaction pressure between 11.9 and 12.6 bar and the $H_2$/$CS_2$ molar ratio between 2.75 and 3.5 (3 being the stoichiometric ratio for the production of $CH_3SH$).

On using a reasonable amount of $H_2S$ present at the start ($H_2S$/$CS_2$ molar ratio=3), the best result gives a degree of conversion of $CS_2$ of 69% and a molar selectivity for $CS_2$ of 65% and for DMS of 35%, which calculations are carried out starting from the molar compositions shown in the patent.

In 1985 and 1969, three patents from Mobil Oil (U.S. Pat. Nos. 4,543,434, 4,822,938, 4,864,074) described processes for the conversion of methane to hydrocarbons of higher molecular weight using intermediate compounds comprising sulfur.

In these patents, the methane is converted to $CS_2$/$H_2S$ by oxidation with sulfur (similar to the Folkins process) and then, under the action of hydrogen, the $CS_2$ is converted to higher hydrocarbons. Without an example being given, the description of these patents mentions that the $CS_2$ is first of all converted to $CH_3SH$ and that the latter is the final intermediate in the direction of the hydrocarbons. Mention is also made that DMS can be coproduced during the reaction between the $CS_2$ and the hydrogen.

The international patent application WO 2004/043883 (Georgia Pacific) for its part describes a process for the catalytic conversion of carbon disulfide to methyl mercaptan in the presence of hydrogen. The catalyst can be $V_2O_5$, $Re_2O_7$ or MnO, supported on a substrate formed of $CeO_2$, $ZrO_2$, $TiO_2$, $Nb_2O_5$, $Al_2O_3$, $SiO_2$, $Ta_2O_5$ or $SnO_2$, or mixtures of these.

Mention is made of a high degree of conversion of $CS_2$ and of a high selectivity for $CH_3SH$ but also of the formation of byproducts, such as $CH_4$, $C_2H_6$, and the like, and also DMS. In addition, this application does not provide any concrete example, and no precise value for conversion or for selectivity is presented.

This review of the prior art makes it possible to observe, on the one hand, the low number of publications relating to the reaction for the catalytic hydrogenation of $CS_2$ to methyl mercaptan and, on the other hand, the lack of information in order to carry out this reaction with high degrees of conversion and high selectivities for methyl mercaptan.

The existing data show, for example, that selectivities for $CH_3SH$ of greater than 65%, under industrially acceptable conditions, have never been obtained.

Consequently, an objective of the present invention is to provide a reaction for the catalytic hydrogenation of sulfur-comprising compounds carrying at least one double bond, especially of C=S type, and in particular for the hydrogenation of carbon disulfide to give methyl mercaptan, which is easy and economic to implement industrially, in particular with low variable costs.

Another objective of the invention is to provide such a reaction which produces only very little or no byproduct, that is say which provides high degrees of conversion, and a high selectivity for hydrogenated product, in particular methyl mercaptan, in other words a process which exhibits enhanced performances in terms of yield, conversion, selectivity and productive output.

Another objective of the invention is to provide a process for the conversion of $CS_2$ to $CH_3SH$ which produces low emissions of carbon dioxide ($CO_2$).

Yet further objectives will become apparent during the account which follows.

The inventors have now discovered that these objectives can be achieved, in all or part, by virtue of the process of the invention which follows and in particular by virtue of a type of specific catalyst which forms a first subject matter of the present invention.

Thus, the present invention relates first of all to a hydrogenation catalyst comprising at least one metal doped with at least one alkali metal or alkaline earth metal hydroxide or oxide.

The metal present in the catalyst of the invention can be any metal from Group 6 and/or 8 of the Periodic Table of the Elements (IUPAC) and is preferably chosen from the group consisting of nickel (Ni), cobalt (Co), palladium (Pd), rhodium (Rh), platinum (Pt), molybdenum (Mo), tungsten (W), chromium (Cr), iron (Fe) and the combinations of two or more of them, preferably the combinations of two of these metals, in particular Co/Mo, Ni/Mo, Ni/W and W/Mo, the combinations of nickel and molybdenum being very particularly preferred.

The metal or metals present in the catalyst of the invention are generally provided in the form of oxides and are available commercially or else are easily prepared from procedures known to a person skilled in the art.

A very particularly preferred catalyst is the catalyst sold by Axens under the name HR 448, which is a combination of nickel oxide (NiO) and of molybdenum oxide ($MoO_3$), supported on high-purity alumina. This catalyst can be used in combination with other catalysts of Ni/Mo and/or Co/Mo type. In addition, this catalyst, like any catalyst of the invention can be presulfurized, as indicated below.

The metal or metals present in the catalyst of the invention can also be provided directly in the form of metal sulfides. These metal sulfides can also be obtained from the corresponding oxides according to any method known to a person skilled in the art, for example as described by van Venrooy in the abovementioned patent U.S. Pat. No. 3,488,739.

The catalyst of the invention is advantageously supported, conventionally, on any type of support generally used in this field, for example on a support chosen from alumina, silica, titanium dioxide ($TiO_2$), zeolites, charcoal, zirconia, magnesia (MgO), clays, hydrotalcites and others, and the mixtures of two or more of them.

The catalyst of the invention is characterized in that it is doped, before use, with at least one alkali metal and/or alkaline earth metal oxide and/or hydroxide, the amount of doping agent generally being between 1 and 30% by weight, preferably between 5 and 20% by weight and advantageously between 8 and 14% by weight of alkali metal and/or alkaline earth metal oxide and/or hydroxide, with respect to the total weight of the catalyst.

The doping indicated above can be carried out according to any method known to a person skilled in the art, for example by dry impregnation with at least one alkali metal and/or alkaline earth metal hydroxide and/or oxide, in particular potassium hydroxide and/or potassium oxide.

According to a preferred embodiment of the invention, the doping is carried out by dry impregnation with a solution of potassium hydroxide (KOH) and/or potassium oxide ($K_2O$).

The catalyst of the invention (metal doped with an alkali metal and/or alkaline earth metal hydroxide and/or oxide) has been shown to be particularly effective in hydrogenation reactions, in particular reactions for the hydrogenation of sulfur-comprising compounds, more particularly sulfur-comprising compounds carrying at least one C=S group. The catalyst of the invention is more particularly effective in the reaction for the catalytic hydrogenation of $CS_2$ to give methyl mercaptan, for which high conversions of $CS_2$ and high selectivities for $CH_3SH$, in particular of the order of 100%, have been observed.

The catalyst of the invention, in particular when it is composed of metal oxide(s), is advantageously pretreated (presulfurized) before being used, in particular in the reaction for the catalytic hydrogenation of $CS_2$ to $CH_3SH$. The pretreatment consists in converting the metal oxide(s) to the corresponding sulfides, for example according to the instructions provided by van Venrooy (U.S. Pat. No. 3,488,739).

By way of illustrative and nonlimiting example, the catalyst of the invention can be pretreated (presulfurized) with a hydrogen/hydrogen sulfide ($H_2/H_2S$) mixture, in the proportions, for example, of 20/80 by moles (or volume). The pretreatment is carried out at a temperature of between 200° C. and 400° C., preferably at a temperature of approximately 300° C., for a time sufficient to provide a conversion of greater than 80%, preferably of greater than 90%, more preferably a complete conversion, of the metal oxides to the corresponding sulfides, i.e. a time of approximately 4 hours for a complete conversion.

The catalyst is then ready to be directly involved in a catalytic hydrogenation reaction. The catalyst, doped and pretreated as indicated above, thus constitutes a subject matter of the present invention. Another subject matter of the present invention is the use of the catalyst as defined above as hydrogenation reaction catalyst, in particular as catalyst for the hydrogenation of sulfur-comprising compounds, more particularly for the catalytic hydrogenation of $CS_2$ to give methyl mercaptan.

According to a third subject matter, the present invention relates to a process for the catalytic hydrogenation of an organic compound carrying at least one unsaturation, preferably at least one C=S functional group, preferably carbon disulfide, said process being characterized in that the hydrogenation catalyst is a catalyst such as that defined above, that is to say a catalyst comprising at least one metal from Group 6 and/or 8 of the Periodic Table of the Elements doped with at least one alkali metal and/or alkaline earth metal oxide and/or hydroxide.

More particularly, the process according to the invention comprises at least the following stages:
a) bringing the organic compound carrying at least one unsaturation, preferably at least one C=S functional group, the organic compound preferably being carbon disulfide, into contact with hydrogen in the presence of at least one catalyst as defined above which has optionally been subjected to the pretreatment for the conversion of the metal oxides to metal sulfides, as described above;
b) carrying out the reaction under hydrogen pressure at a temperature of between 100° C. and 400° C., preferably of between 200° C. and 300° C.; and
c) recovering the hydrogenation product, i.e. methyl mercaptan when the starting material is carbon disulfide, with separation of the $H_2S$ formed.

According to a preferred embodiment of the invention, in the case of the reaction for the catalytic hydrogenation of carbon disulfide to give methyl mercaptan, the $H_2/CS_2$ molar ratio, which can vary within wide limits, is generally between 1:1 and 50:1.

The various tests carried out by the inventors show that the greater the amount of hydrogen, with respect to the amount of $CS_2$ introduced, the more the productive output, with respect to a given volume of catalyst, decreases. Consequently, it is preferable to operate with an $H_2/CS_2$ ratio of between 1:1 and 30:1, preferably between 1:1 and 10:1, more preferably between 2:1 and 9:1. Ratios approximately equal to 3:1, 6:1 and 9:1 have provided very good results, the best results being obtained for an $H_2/CS_2$ ratio of between 3:1 and 6:1.

The amount of catalyst can also vary within very wide limits. This is because it is directly related to the productive output desired. Generally, the productive output is expressed as amount of methyl mercaptan produced per unit of time and per unit of volume of catalyst (or unit of weight of catalyst).

As a general rule, the amount of catalyst is set according to the nature and amount of the compound to be hydrogenated. Thus, an amount of 0.5 to 6 kg/hour/liter of catalyst of compound to be hydrogenated, in particular of carbon disulfide, is sufficient, indeed even optimal, for a hydrogenation reaction to give methyl mercaptan.

It is also possible to use a compound which is inert with regard to the catalyst in order to dilute the reaction exotherm. Such an inert compound is well known to a person skilled in the art who is a specialist in catalytic hydrogenation reactions and can, for example, be carborundum (silica carbide).

As indicated above, the hydrogenation reaction is carried out under hydrogen pressure. The pressure necessary for the reaction can, here again, vary within wide limits. It is generally between atmospheric pressure and 100 bar (approximately 10 MPa), preferably between atmospheric pressure and 50 bar (approximately 5 MPa) and more preferably between atmospheric pressure and 30 bar (3 MPa). According to an entirely preferred aspect, the hydrogen pressure is between 3 bar (0.3 MPa) and 15 bar (1.5 MPa).

The hydrogen pressure has, inter alia, an important effect on the contact time between the reactants and the catalyst. A high pressure and thus a high contact time can prove to be beneficial for the conversion of the substrate (in this instance $CS_2$). However, excessively high contact times can also promote side reactions; this is why a compromise has to be found for optimal performances.

The reaction for the catalytic hydrogenation of carbon disulfide to give methyl mercaptan can be carried out in the presence of hydrogen sulfide, which is itself formed during the reaction. An amount of hydrogen sulfide which can range up to 10 $H_2S$ per 1 $CS_2$ in moles does not have an effect on the productive output, the yield, the degree of conversion and the selectivity of the reaction.

The reaction temperature is generally between 100° C. and 400° C., preferably between 200° C. and 300° C., as was mentioned above. It has been observed that an excessively high temperature has a harmful effect on the selectivity, with formation of byproducts not desired in the context of the present invention, such as methane and dimethyl sulfide. On the other hand, an excessively low temperature results in a fall in conversion of the product to be hydrogenated, typically carbon disulfide.

The catalyst according to the invention can be used, in particular in the abovementioned hydrogenation reactions, according to any method known in the field, for example in a fixed, fluid, circulating or ebullating bed. In the examples illustrating the invention, the catalyst has been used in a fixed bed.

Likewise, while all the types of hydrogenation reactors can be envisaged for the hydrogenation reaction according to the present invention, preference is given to the reactors which make possible good heat exchanges, in order to be able to remove the heat of the reaction as efficiently as possible.

The reaction time varies according to the nature and the amount of the product to be hydrogenated, the amount of hydrogen and the nature and the amount of catalyst used. This time is generally very short, for example of the order a second, which renders the process of the invention entirely suitable for carrying out the reaction continuously.

The reaction is advantageously carried out without solvent and without water. In addition, if necessary or desired, it can be carried out in the presence of an inert gas, such as nitrogen, argon and others.

The hydrogenated compound obtained on conclusion of the reaction, methyl mercaptan in the case of the hydrogenation of carbon disulfide, can be separated from the crude reaction product according to any conventional means known to a person skilled in the art, for example by condensation, by cooling, optionally by increase in pressure.

The process of the invention, advantageously carried out continuously, makes it possible in particular to carry out the hydrogenation of carbon disulfide with a high productive output, a high degree of conversion of carbon disulfide and a high selectivity for methyl mercaptan, that is to say an exclusive or virtually exclusive formation of methyl mercaptan, without observing the formation of the undesirable byproducts normally formed with the processes described in the prior art.

The characteristics set out above render the process particularly suitable for the industrial production of $CH_3SH$ of high purity by catalytic hydrogenation of carbon disulfide, in particular the production of $CH_3SH$ with a purity of greater than 99.9%, with impurities in negligible amounts which are below the detection thresholds and in particular of less than 1000 ppm.

The present invention is now illustrated by means of the following examples, which do not exhibit any limiting nature and which consequently cannot be understood as capable of restricting the scope of the invention as claimed.

For each of the examples, the reaction products and the unreacted materials are vaporized and analyzed in line by gas chromatography with a nonpolar capillary column and a thermal conductivity cell as detector, after calibrating for each product with pure samples.

The degrees of conversion, selectivity and productive output are calculated in the following way (for each calculation, the number of moles of product i is equal to the molar flow rate of the product i multiplied by unit of time):

Degree of Conversion of $CS_2$ (% C):
If $n_{0\ CS_2}$ is the starting number of moles of $CS_2$ and $n_{residual\ CS_2}$ is the number of moles of unreacted $CS_2$, the degree of conversion of $CS_2$ (% C) can be calculated according to the following equation:

$$\% \ C = \frac{n_{0CS_2} - n_{residual\ CS_2}}{n_{0CS_2}} \times 100$$

Molar Selectivity for $CH_3SH$ (% $S_{CH_3SH}$):
If $n_{CH_3SH}$ is the number of moles of $CH_3SH$ produced during the reaction, the molar selectivity for $CH_3SH$ (% $S_{CH_3SH}$) can be calculated according to the following equation:

$$\% \ S_{CH_3SH} = \frac{n_{CH_3SH}}{n_{0CS_2} - n_{residual\ CS_2}} \times 100$$

Molar Selectivity for $CH_4$ (% $S_{CH_4}$):
The molar selectivity for methane (% $S_{CH_4}$) can also be calculated from the following equation:

$$\% \ S_{CH_4} = \frac{n_{CH_4}}{n_{0CS_2} - n_{residual\ CS_2}} \times 100$$

Molar Selectivity for Dimethyl Sulfide (% $S_{DMS}$):
Likewise, the molar selectivity for DMS (% $S_{DMS}$) is calculated by using the following equation:

$$\% \ S_{DMS} = \frac{2 \times n_{DMS}}{n_{0CS_2} - n_{residual\ CS_2}} \times 100$$

$CH_3SH$ Productive Output (% $P_{CH_3SH}$):
The methyl mercaptan productive output is then calculated from the following equation (where $M_{CH_3SH}$ and $M_{CS_2}$ respectively represent the molar mass of $CH_3SH$ and the molar mass of $CS_2$:

$$P_{CH_3SH} = \text{flow rate by weight of } CS_2 \times \% \ C \times \% \ S_{CH_3SH} \times \frac{M_{CH_3SH}}{M_{CS_2}}$$

where the flow rate by weight of $CS_2$ is expressed in tonnes/day/$m^3$ of catalyst.

EXAMPLE 1

Preparation of Catalysts

The tests are carried out on four catalysts, an undoped catalyst (Cata 1, comparative example) and three catalysts doped with different amounts of potassium oxide (Cata 2: 5.8%; Cata 3: 11.6% and Cata: 17.4% by weight).

Cata 1 is the commercial catalyst HR 448 from Axens (3.3% of nickel oxide and 16.5% of molybdenum trioxide on an alumina support). The other three catalysts (according to the invention) are prepared according to the following procedure.

For each catalyst Cata 2, Cata 3 and Cata 4, 100 ml (79 g) of catalyst HR 448 (Axens), dried beforehand at 150° C. overnight, are introduced into a rotary evaporator.

At the same time, a potassium hydroxide solution is prepared by dissolving 5.80 g of potassium hydroxide (KOH) in 38.6 ml of demineralized water. This volume corresponds to the pore volume of the 79 g of HR 448 (determined beforehand with demineralized water on a representative sample of the batch of catalyst used). For the high concentrations (17.4% $K_2O$), the potassium hydroxide is dissolved in hot water.

The solution is introduced slowly and continuously into the rotary evaporator (a slight vacuum allows the solution to be introduced by pressure difference). Throughout the introduction, the receptacle containing the catalyst is gently rotated, in order to promote homogeneous impregnation.

The impregnation operation is carried out is maintained at ambient temperature, in order to prevent any evaporation of water before the end of the introduction of the solution.

At the end of the introduction, the water is removed under vacuum and while heating at 100° C. After this "in situ" drying, the impregnated catalyst Cata 2 is calcined at 500° C. for 2 hours and is then ready to be used, after cooling.

According to a similar procedure, Cata 3 is obtained from 12.35 g of KOH, to result in a doped catalyst comprising 11.6% of $K_2O$, and Cata 4 is obtained in a similar way from 19.82 g of KOH, to result in a doped catalyst comprising 17.4% of $K_2O$.

The catalysts (comprising metal oxides) are subjected to the following pretreatment: 30 ml of catalyst are introduced into a tubular reactor. The catalyst is then brought into contact with a mixture of $H_2S$ (8 Standard liters/hour) and $H_2$ (2 Standard liters/hour) at 400° c for 4 hours. The pressure in the tubular reactor is set at a value identical to that of the hydrogenation reaction, between 3 bar (0.3 MPa) and 15 bar (1.5 MPa), for example 3 bar (0.3 MPa).

The sulfurized catalysts are recovered and used directly in the hydrogenation reactions exemplified below.
Reactions for the hydrogenation of $CS_2$ to give $CH_3SH$

EXAMPLE 2

Study of the Effect of the Doping

The catalysts obtained in example 1 (Cata 2, Cata 3 and Cata 4) are used directly after the pretreatment with sulfur. Cata 1 (undoped catalyst which has also been subjected to the pretreatment with sulfur) is used as comparative example. The amount of catalyst used is generally 30 ml, some tests having been carried out with 6 ml and 10 ml of catalyst. In addition, in some tests carried out with 6 ml of catalyst, said catalyst was diluted to 30 ml with an inert compound (carborundum).

The $H_2$ and $H_2S$ flow rates are adjusted in order to correspond to the molar ratio required for $CS_2$; for example, for an $H_2S/CS_2$ molar ratio equal to 2 and an $H_2S/CS_2$ molar ratio equal to 6, the $CS_2$ flow rate is equal to 11.3 g/h (149 mmol/h, i.e. 3.3 Standard gas liters/h).

Various tests are carried out with an $H_2/CS_2$ molar ratio of between 3 and 9. The $CS_2$ flow rate to be applied as a function of the $H_2/CS_2$ ratio chosen is given in the following table 1 as illustrative examples.

TABLE 1

| $H_2/CS_2$ ratio | $CS_2$ flow rate |
|---|---|
| 3 | 17 g/h (567 g/h/liter of catalyst) |
| 6 | 11.3 g/h (377 g/h/liter of catalyst) |
| 9 | 7.5 g/h (250 g/h/liter of catalyst) |
| 30 | 2 g/l (67 g/h/liter of catalyst) |

The $CS_2$ flow rate is modified with the $H_2/CS_2$ molar ratio in order to maintain a residence time which is always identical. The $H_2$ flow rate can be easily deduced when the molar ratio is known. Thus, in the example where the $H_2/CS_2$ molar ratio is 6 (see above) and the $CS_2$ flow rate is 11.3 g/h, i.e. 3.3 Standard gas liters/h, the hydrogen $H_2$ flow rate is equal to 6 times this $CS_2$ flow rate, i.e. 20 Standard liters per hour. Likewise, the $H_2S$ flow rate can easily be deduced when the molar ratio is known. Thus, in the same way as with the hydrogen in the above example, an $H_2S/CS_2$ molar ratio of 2 means that the $H_2S$ flow rate is equal to twice the gas flow rate by volume of the $CS_2$, i.e., in this instance, 6.6 Standard liters per hour (twice 3.3).

At the same time, the tubular reactor is cooled to the temperature desired for the hydrogenation reaction, that is say between 200° C. and 300° C., for example 250° C. The $CS_2$ is introduced only when all the flow rates and the temperature have stabilized.

At the outlet of the reactor, all the reaction products and the unreacted materials are vaporized and analyzed in line by gas chromatography.

For the various tests carried out with the doped catalysts (Cata 2, Cata 3 and Cata 4), no formation of methane or of dimethyl sulfide is observed. The gases resulting the reactor also do not comprise unreacted $CS_2$. It can thus be concluded that the degree of conversion of $CS_2$ is 100% and the selectivity for $CH_3SH$ is 100%.

The operational and analytical data for the various tests are collated in the following table 2:

TABLE 2

| General operating conditions: | | | | |
|---|---|---|---|---|
| Catalyst volume: | | | 30 ml | |
| Reaction temperature: | | | 250° C. | |
| Reaction pressure (MPa): | | | 0.3 | |
| $H_2/CS_2$ molar ratio: | | | 6 | |
| $H_2S/CS_2$ molar ratio: | | | 2 | |

| | Test No. | | | |
|---|---|---|---|---|
| | 2.1 | 2.2 | 2.3 | 2.4 |
| | | Catalyst | | |
| | Cata 1 | Cata 2 | Cata 3 | Cata 4 |
| $CS_2$ flow rate (g/h) | 10.0 | 11.3 | 11.3 | 11.3 |
| $CS_2$ conversion (%) | 100 | 100 | 100 | 55 |
| $CH_3SH$ selectivity (%) | 29 | 71 | 100 | 100 |
| $CH_4$ selectivity (%) | 37 | 21 | 0.0 | 0.0 |
| DMS selectivity (%) | 34 | 7 | 0.0 | 0.0 |

The above results show the effect of the doping of the hydrogenation catalyst on the selectivity for methyl mercaptan. Although the absence of doping makes possible complete conversion of $CS_2$, the hydrogenation reaction is not at all selective: methyl mercaptan, methane and dimethyl sulfide are formed in substantially equal amounts.

On the other hand, the doping of the catalyst makes it possible to considerably increase the selectivity of methyl mercaptan up to 100% with 11.6% of $K_2O$ doping agent and above. It is also found that an increase in the degree of doping results in a loss in conversion of the carbon disulfide.

EXAMPLE 3

Study of the Effect of the Temperature

Tests on the catalytic hydrogenation of carbon disulfide to give methyl mercaptan are carried out, according to the procedure described in example 2 above, at different temperatures (200° C., 250° C. and 300° C.).

The operational and analytical data of these three tests are collated in the following table 3:

TABLE 3

| General operating conditions: | | | |
|---|---|---|---|
| Catalyst: | Cata 3 | | |
| Catalyst volume: | 30 ml | | |
| $CS_2$ flow rate (g/h): | 11.3 | | |
| Reaction pressure (MPa): | 0.3 | | |
| $H_2/CS_2$ molar ratio: | 6 | | |
| $H_2S/CS_2$ molar ratio: | 2 | | |
| | Test No. | | |
| | 3.1 | 3.2* | 3.3 |
| Reaction temperature (° C.) | 200 | 250 | 300 |
| $CS_2$ conversion (%) | 31.6 | 100 | 100 |
| $CH_3SH$ selectivity (%) | 100 | 100 | 70.6 |
| $CH_4$ selectivity (%) | 0.0 | 0.0 | 29.4 |
| DMS selectivity (%) | 0.0 | 0.0 | 0.0 |

*corresponds to test 2.3

The results of these tests show that the temperature has only a slight effect on the hydrogenation reaction, in particular as regards the selectivity for methyl mercaptan. Even at a reaction temperature of 300° C., little methane is formed and no trace of DMS could be demonstrated.

EXAMPLE 4

Study of the Effect of the $H_2/CS_2$ Ratio

Similarly to example 2 above, various tests on the catalytic hydrogenation of carbon disulfide to methyl mercaptan are carried out, this time varying the amount of hydrogen introduced. The $H_2/CS_2$ molar ratio was set at 3, 6 and 9 respectively.

The operational and analytical data of these three tests are collated in the following table 4:

TABLE 4

| General operating conditions: | |
|---|---|
| Catalyst: | Cata 3 |
| Catalyst volume: | 30 ml |
| $CS_2$ flow rate (g/h): | 11.3 |
| Reaction pressure (MPa): | 0.3 |
| Reaction temperature (° C.): | 250° C. |
| $H_2S/CS_2$ molar ratio: | 2 |

TABLE 4-continued

| General operating conditions: | | | |
|---|---|---|---|
| | Test No. | | |
| | 4.1 | 4.2* | 4.3 |
| $H_2/CS_2$ ratio | 3 | 6 | 9 |
| $CS_2$ conversion (%) | 83.6 | 100 | 100 |
| $CH_3SH$ selectivity (%) | 100 | 100 | 100 |
| $CH_4$ selectivity (%) | 0.0 | 0.0 | 0.0 |
| DMS selectivity (%) | 0.0 | 0.0 | 0.0 |

*corresponds to test 2.3

The above results show that, with an $H_2/CS_2$ ratio equal to 3, the amount of hydrogen is insufficient to convert all the carbon disulfide. On the other hand, for all the ratios 3, 6 and 9, the selectivity for methyl mercaptan is 100%, this being by virtue of the doping of the catalyst in accordance with the invention.

EXAMPLE 5

Study of the Effect of the Reaction Pressure

Similarly to example 2 above, various tests on the catalytic hydrogenation of carbon disulfide to give methyl mercaptan are carried out, this time varying the pressure applied to the reaction medium as function of the temperature. The pressures tested are 0.3 MPa and 1.5 MPa and the reaction temperatures tested are 200° C. and 250° C.

The operational and analytical data of these tests are collated in the following table 5.

TABLE 5

| General operating conditions: | | | | |
|---|---|---|---|---|
| Catalyst: | Cata 3 | | | |
| Catalyst volume: | 30 ml | | | |
| $CS_2$ flow rate (g/h): | 11.3 | | | |
| $H_2/CS_2$ molar ratio: | 6 | | | |
| $H_2S/CS_2$ molar ratio: | 2 | | | |
| | Test No. | | | |
| | 5.1* | 5.2 | 5.3** | 5.4 |
| Reaction pressure (MPa) | 0.3 | 1.5 | 0.3 | 1.5 |
| Reaction temperature (° C.) | 200 | 200 | 250 | 250 |
| $CS_2$ conversion (%) | 31.6 | 100 | 100 | 100 |
| $CH_3SH$ selectivity (%) | 100 | 100 | 100 | 82.9 |
| $CH_4$ selectivity (%) | 0.0 | 0.0 | 0.0 | 17.1 |
| DMS selectivity (%) | 0.0 | 0.0 | 0.0 | 0.0 |

*corresponds to test 3.1
**corresponds to test 2.3

The above results show that, at high temperature and high pressure, complete conversion of $CS_2$ is retained but with formation of methane. All the tests clearly show the absence of formation of DMS in each of the cases.

What is claimed is:

1. A process for conducting a hydrogenation reaction which comprises using at least one hydrogenation catalyst comprising at least one metal doped with at least one alkali metal or alkaline earth metal hydroxide or oxide as catalyst of the hydrogenation reaction for the hydrogenation of sulfur-comprising compounds having C═S functional groups,
wherein the amount of alkali metal and/or alkaline earth metal oxide and/or hydroxide, with respect to the total weight of the catalyst, is between 1 and 30% by weight.

2. The process as claimed in claim 1, in which the catalyst comprises nickel and molybdenum, is supported on alumina and is doped with potassium hydroxide or potassium oxide.

3. A process for the catalytic hydrogenation of an organic compound carrying at least one C=S functional group which comprises using at least one hydrogenation catalyst comprising at least one metal doped with at least one alkali metal or alkaline earth metal hydroxide or oxide as catalyst.

4. The process as claimed in claim 3, comprising at least the following stages:
  a) bringing the organic compound carrying the at least one C=S functional group into contact with hydrogen in the presence of the at least one hydrogenation catalyst which has optionally been subjected to a pretreatment for the conversion of the metal oxides to metal sulfides;
  b) carrying out the reaction under hydrogen pressure at a temperature of between 100° C. and 400° C. or between 200° C. and 300° C.; and
  c) recovering the hydrogenation product.

5. The process as claimed in claim 4, which is a process for the catalytic hydrogenation of carbon disulfide to give methyl mercaptan.

6. The process as claimed in claim 5, in which the $H_2/CS_2$ ratio is between (a) 1:1 and 30:1, (b) 1:1 and 10:1, (c) 2:1 and 9:1, or (d) 3:1 and 6:1.

7. The process as claimed in claim 5, wherein it is carried out continuously.

8. The process as claimed in claim 5, wherein it is carried out without solvent and without water and optionally in the presence of an inert gas, such as nitrogen, argon and others.

9. The process as claimed in claim 5, wherein the conversion of carbon disulfide is 100% and the selectivity for methyl mercaptan is 100%.

10. The process as claimed in claim 1, wherein the metal is (1) a metal of Group 6 or Group 8 of the Periodic Table of the Elements, (2) selected from the group consisting of nickel (Ni), cobalt (Co), palladium (Pd), rhodium (Rh), platinum (Pt), molybdenum (Mo), tungsten (W), chromium (Cr), iron (Fe) and the combinations of two or more of them, or (3) Co/Mo, Ni/Mo, Ni/W and W/Mo.

11. The process as claimed in claim 1, wherein the metal is a combination of nickel and molybdenum.

12. The process as claimed in claim 1, wherein the metal is present in the oxide or sulfide form.

13. The process as claimed in claim 1, wherein the catalyst is supported on a support selected from the group consisting of alumina, silica, titanium dioxide, zeolites, charcoal, zirconia, magnesia (MgO), clays, hydrotalcites and others, and the mixtures of two or more of them.

14. The process as claimed in claim 1, wherein the amount of alkali metal and/or alkaline earth metal oxide and/or hydroxide, with respect to the total weight of the catalyst, is between 5 and 20% by weight.

15. The process as claimed in claim 1, wherein the doping agent is potassium hydroxide or potassium oxide.

16. The process as claimed in claim 3, wherein the metal is (1) a metal of Group 6 or Group 8 of the Periodic Table of the Elements, (2) selected from the group consisting of nickel (Ni), cobalt (Co), palladium (Pd), rhodium (Rh), platinum (Pt), molybdenum (Mo), tungsten (W), chromium (Cr), iron (Fe) and the combinations of two or more of them, or (3) Co/Mo, Ni/Mo, Ni/W and W/Mo.

17. The process as claimed in claim 3, wherein the metal is a combination of nickel and molybdenum.

18. The process as claimed in claim 3, wherein the metal is present in the oxide or sulfide form.

19. The process as claimed in claim 3, wherein the catalyst is supported on a support selected from the group consisting of alumina, silica, titanium dioxide, zeolites, charcoal, zirconia, magnesia (MgO), clays, hydrotalcites and others, and the mixtures of two or more of them.

20. The process as claimed in claim 3, wherein the amount of alkali metal and/or alkaline earth metal oxide and/or hydroxide, with respect to the total weight of the catalyst, is between (a) 1 and 30% by weight, (b) 5 and 20% by weight, or (c) 8 and 14% by weight.

21. The process as claimed in claim 3, wherein the doping agent is potassium hydroxide or potassium oxide.

22. The process as claimed in claim 3, wherein the hydrogenation catalyst comprises nickel and molybdenum, is supported on alumina, and is doped with potassium hydroxide or potassium oxide.

23. The process as claimed in claim 1, wherein the hydrogenation reaction is the catalytic hydrogenation of $CS_2$ to give methyl mercaptan.

24. The process as claimed in claim 1, wherein the amount of alkali metal and/or alkaline earth metal oxide and/or hydroxide, with respect to the total weight of the catalyst, is between 8 and 14% by weight.

\* \* \* \* \*